United States Patent [19]
Kieval et al.

[11] Patent Number: 6,073,048
[45] Date of Patent: Jun. 6, 2000

[54] BAROREFLEX MODULATION WITH CAROTID SINUS NERVE STIMULATION FOR THE TREATMENT OF HEART FAILURE

[75] Inventors: Robert S. Kieval, Golden Valley; Tom D. Bettett, Shoreview; Stephanie Michele Fitts, St. Louis Park, all of Minn.

[73] Assignee: Medtronic, Inc., Minneapolis, Minn.

[21] Appl. No.: 08/559,957

[22] Filed: Nov. 17, 1995

[51] Int. Cl.[7] .................................................. A61N 1/365
[52] U.S. Cl. .................................................. 607/17; 607/2
[58] Field of Search .................................. 607/2, 3, 4, 5, 607/6, 7, 8, 9, 10, 14, 15, 16, 17, 18, 19, 20, 21, 22, 23, 24

[56] References Cited

U.S. PATENT DOCUMENTS

| | | |
|---|---|---|
| 3,421,511 | 1/1969 | Schwartz . |
| 3,522,811 | 8/1970 | Schwartz . |
| 3,577,315 | 5/1971 | Franklin . |
| 3,650,277 | 3/1972 | Sjostrand . |
| 3,658,053 | 4/1972 | Fergusson . |
| 3,710,778 | 1/1973 | Cornelius . |
| 4,009,721 | 3/1977 | Alcidi . |
| 4,201,219 | 5/1980 | Gonzales . |
| 4,414,986 | 11/1983 | Dickhudt . |
| 4,467,807 | 8/1984 | Bornzin . |
| 4,716,887 | 1/1988 | Koning . |
| 4,750,495 | 6/1988 | Moore . |
| 4,791,931 | 12/1988 | Slate . |
| 5,111,815 | 5/1992 | Mower . |
| 5,203,326 | 4/1993 | Collins . |
| 5,305,745 | 4/1994 | Zacouto . |
| 5,368,040 | 11/1994 | Carney . |
| 5,411,540 | 5/1995 | Edell . |

FOREIGN PATENT DOCUMENTS 9216257  10/1992  WIPO .

*Primary Examiner*—Scott M. Getzow
*Attorney, Agent, or Firm*—Harold R. Patton; Reed A. Duthler

[57] ABSTRACT

A system and method for stimulating the baroreflex arc based on levels of indicators from the body includes a pacemaker for bradycardia support pacing should the indicators show the need for support pacing. Other indicators and a process take advantage of an assumed relationship between peripheral vascular resistance and pulmonary resistance to determine the level of nerve stimulation required. This level is adjusted or optimized based on its interaction with heart activity and changes in the other indicators. These other indicators are readily available to the implanted device and allow for a process to make an estimate of pulmonary vascular resistance, from which SVR is also estimated. The value determined for SVR is the primary value used to determine the level of nerve stimulation absent indicators for the need to provide bradicardia pacing. The pacemaker can be rate responsive, as can the process for determining the level of nerve stimulation to be delivered. Several different lead configurations are described.

21 Claims, 8 Drawing Sheets

BAROREFLEX MODULATION WITH CAROTID SINUS NERVE STIMULATION FOR THE TREATMENT OF HEART FAILURE

This invention is related to Central Nerve stimulation by implanted devices and has particular application to using closed loop feedback techniques to improve its activity. It is potentially useful for patients with congestive heart failure including cases caused by coronary artery disease, myocardial infraction and chronic hypertension but not limited to these causes.

Congestive heart failure (CHF) represents a major unmet medical need. It is a disease with a high incidence and prevalence, high morbidity and mortality, and except for heart transplantation, no definitive treatment. It is estimated that 2–3 million people in just the United States suffer from congestive heart failure, with over 400,000 new cases diagnosed each year. CHF is the leading cause of hospitalization in the United States in patients over 65. The major causes of CHF are coronary artery disease and hypertension. CHF may also result from valvular disease, conduction system disturbances, congenital heart defects, cardiomyopathies or other problems. Patients suffering from CHF may experience weakness, fatigue, labored breathing, water retention in the extremities, exercise intolerance and dizziness. These patients may require repeated hospitalizations and intensive care admissions for close monitoring and supervision. Mean survival after a diagnosis of CHF is 5 years. The annual mortality rate of patients with advanced heart failure may approach 50%.

Annual health care expenditures for CHF in the United States are estimated to exceed $37 billion. Standard medical intervention incompletely controls patient symptoms or is associated with significant side effects, and morbidity and mortality remain high despite optimal care. For patients refractory to conventional medical therapy, heart transplant is the only available treatment.

CHF is defined as a condition in which the heart does not pump enough blood to meet the body's needs. The patient's response to this disorder is complex and includes activation of the sympathetic nervous system, renin-angiotensin system and other neuroendocrine systems. The increased sympathetic nervous system drive and circulating levels of neurohormonal mediators (e.g., angiotensin II) may help the cardiovascular system compensate by resulting in a stronger and faster heart beat coupled with an increase in the blood pressure (by peripheral vasoconstriction) to improve organ perfusion. In the failing heart, however, this normal neurohormonal activation response is associated with accelerated myocardial damage and poor patient prognosis. Consequently, current pharmacological strategies for CHF focus on reducing neurohormonal activation (for example, with ACE inhibitors) or blocking its effects at the tissue level (for example, with beta-adrenergic receptor blockers, angiotensin II receptor blockers, etc.). These approaches can alleviate patient symptoms, improve survival, and delay or prevent the onset of CHF in asymptomatic patients with left ventricular dysfunction.

Reflex control of the heart and peripheral vasculature is provided in part by baroreceptors. These nerve bundles detect changes in blood pressure and are located in the carotid sinus in the patient's neck region the aortic arch, as well as other areas. The baroreceptors respond to increases or decreases in arterial blood pressure by firing more or less frequently, respectively. The carotid sinus nerves transmit these impulses to the brain which modifies heart rate and vasomotor tone as well as changing the concentration of neurohormones by altering the balance of sympathetic and parasympathetic nervous system activation.

Previously, modulation of baroreflex activity by electrical stimulation of carotid sinus nerves has been advocated as a treatment for hypertension as well as intractable angina pectoris (chest pain associated with myocardial ischemia). CSNS can produce a reduction in heart rate, contractility, arteriolar and venous constriction and blood pressure making it a viable treatment for these ailments. These effects are modulated by increased vagal nerve activity and decreased sympathetic tone to the heart and peripheral vasculature. Reduction of sympathetic tone achieved through Carotid Sinus Nerve Stimulation (CSNS), results in reduction in heart rate (reduced oxygen demand), myocardial contractility (reduced myocardial work), peripheral vasoconstriction (afterload reduction) and renin-angiotensin activity (reduced neurohormonal activation). CSNS may offer a therapeutic advantage in any disorder affecting these blood pressure related systems. Moreover, the sensitivity of the baroreflex receptors is reduced in many patients with CHF, contributing to neuroendocrine dysfunction. CSNS could provide a means for compensating for this deficit.

Pharmacological treatments may have side effects requiring discontinuation of drug therapy in up to 30% of patients in clinical studies. Patient non-compliance to drug regimens also limits the utility of pharmacological agents. By contrast, CSNS therapy would ensure patient compliance, could be closely titrated to each patient's needs and may also give patients the ability to maintain a reduced drug regimen. Ultimately, CSNS may lead to improved functional capacity, quality of life and survival. To date, however, this possibility has been largely unrecognized.

Carotid sinus nerve stimulation is well known through developments at Medtronic, Inc., of Minneapolis, Minn. In the 1960s to early 1970s, Medtronic produced and marketed two carotid sinus nerve stimulators for treatment of hypertension, the "Barostat," and angina, the "Angistat." These devices lowered blood pressure, decreased myocardial work and oxygen consumption, and thereby alleviated hypertension and angina.

The stimulation system consisted of an external pulse generator/transmitter (which could be operated by the patient pushing a button), a receiver implanted in the clavicular region, and implanted nerve electrodes in the neck region. As in many devices of that era, the power source was maintained externally as battery technology was a limiting factor. Moreover, the implanted receiver and electrode were large and relatively unsophisticated by today's standards. Eventually, these therapies were superseded by the advent of effective antihypertension medications and coronary artery revascularization techniques.

While antiarrhythmia pacing has been suggested using nerve stimulation before (see for example U.S. Pat. No. 5,203,326, issued to Collins), as well as blood pressure reduction by this mechanism (see U.S. Pat. No. 3,650,277, issued to Sjostrand) no satisfactory use of CSNS for CHF exists in active treatment today.

The idea of using drug delivery to enhance carotid sinus nerve activity for blood related disorders is shown in U.S. Pat. No. 5,305,745 issued to Zacouto, which also suggests using the ECG as an indicator. Also, ischemia detection has been used to generate CSNS electrical stimulation in an implanted device as described in the PCT publication by Obel, et al. in PCT/US92/02250, October, 1992 under number WO92/16257. Nevertheless, the problem of producing a working device that provides the physician with the ability

SUMMARY OF THE INVENTION

The disclosure herein describes a device which stimulates the baroreflex arc in patients with congestive heart failure. This stimulation is a mechanism for modulating the neurohormonal activation of the patient and thereby alleviating the symptoms of CHF and underlying cause of morbidity and mortality. The implantable system stimulates the patient's nervous system activating the baroreflex which in turn decreases sympathetic and increases parasympathetic activity. In addition, the stimulation has peripheral effects on the vascular resistance, and cardiac effects on the rate, and strength of contraction.

The system can be operated in a closed loop system in which patient parameters(both intra and extra cardiac in origin) are fed back into the system logic and the output is optimized for the patient's condition.

In a most preferred embodiment, the closed loop system provides electrical stimulation to the carotid sinus nerves of the patient through leads extending through the patient's body from an implanted device. The device may have additional leads associated with the patient's heart. The implanted device varies the electrical stimulation provided to the Central Nervous System (CNS) in response to feedback signals generated by the patient's heart and cardiovascular system sensed by the implanted device, thus forming a closed loop feedback system.

Such cardiovascular optimization would result in reduction of long-term cardiac stress by decreasing sympathetic efferent nerve activity, blood pressure, heart rate and strength of contraction(i.e. reduced $O_2$ consumption), peripheral vasoconstriction and neurohormonal activation. Thus, not only would the system alleviate the symptoms associated with congestive heart failure, but it would also act to abate the causative mechanisms of heart failure.

The use of an activity sensor would allow CSNS stimulation to be decreased during periods of activity when an increased heart rate and blood pressure are needed. The lead associated with the patient's heart would be able to provide bradycardia pacing in the event CSNS induced bradycardia or asystole. Additionally, an oxygen and pressure sensor could be associated with this lead to provide additional feedback parameters for stimulation control.

DETAILED DESCRIPTION OF THE PREFERRED EMBODIMENTS

Figure 1:
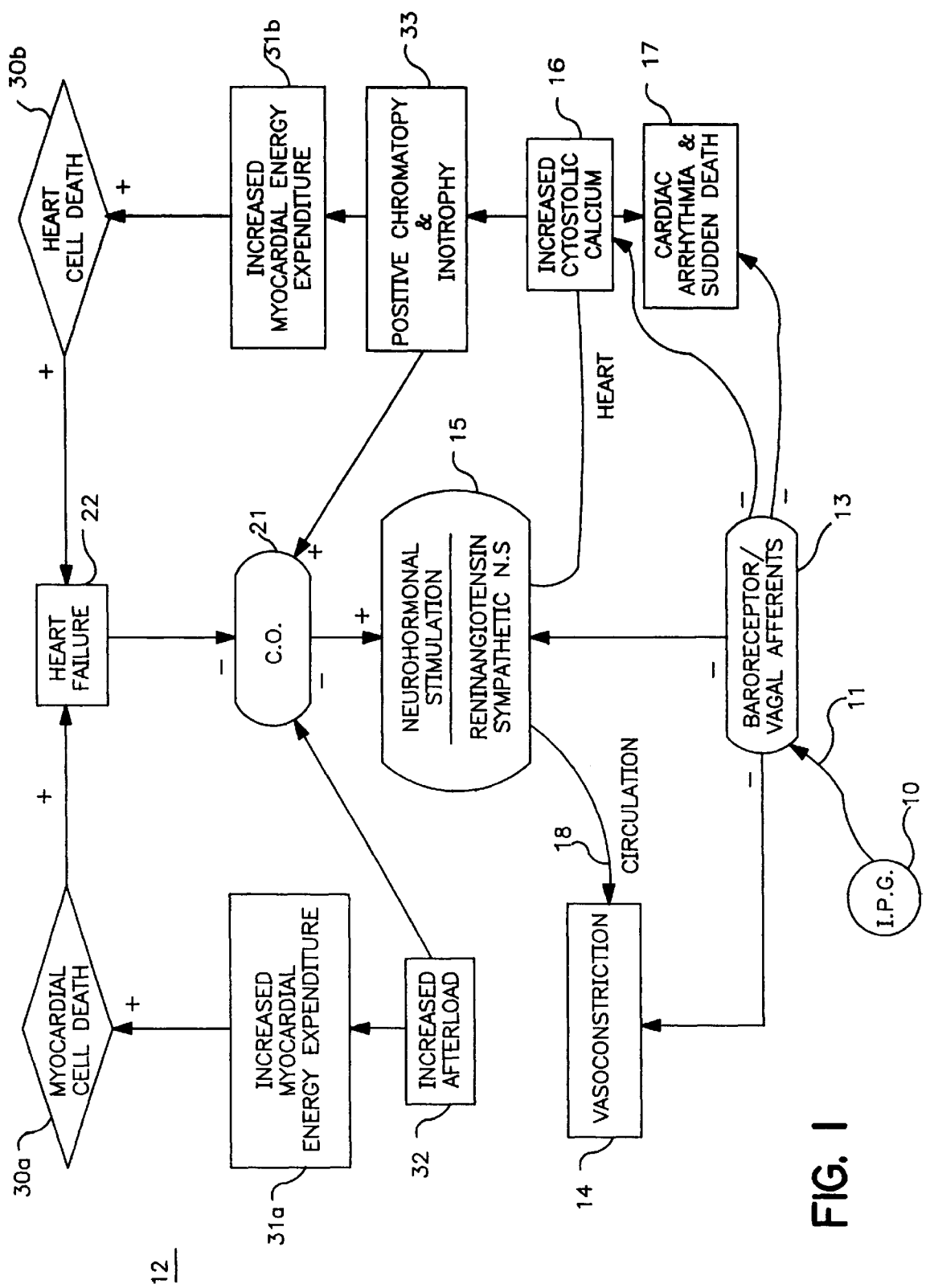
FIG. 1 is a flow chart showing how the stimulation by an implantable pulse generator of carotid sinus or other vagal afferent nerves may affect patients with CHF.

A sense of this invention can be captured with reference to FIG. 1 in which an implanted pulse generating device (IPG) 10 is shown controlling or affecting the human system 12 via stimulation 11 of the carotid sinus baroreceptors/vagal afferent nerves 13. In heart failure (22), inappropriate Sympathetic Nervous System (SNS) activation causes vasoconstriction 14, neurohormonal stimulation 15, increased systolic calcium 16. All of these factors contribute to a progression of the heart failure symptoms including cardiac arrhythmias and sudden death 17. Overdriving the Central Nervous System (CNS) nerves with the IPG (10) can alleviate these factors by decreasing SNS activation. If the human sensor 13 indicates stimulation is needed, stimulation commences and alleviates vasoconstriction (14) which in turn decreases afterload (32), decreases myocardial energy expenditure (31b) and prevents myocardial cell death (30a). The stimulation also acts to decrease the prevalence of cardiac arrhythmias (17), decrease cytosolic calcium levels (16) which decreases chronotropy and inotropy (33), decreases cell energy expenditure (31a) and prevents cell death (30b). Stimulation would also act to decrease neurohormonal stimulation (15) which is inappropriately elevated in CHF and is associated with the reduction in cardiac output (21).

Figure 2:
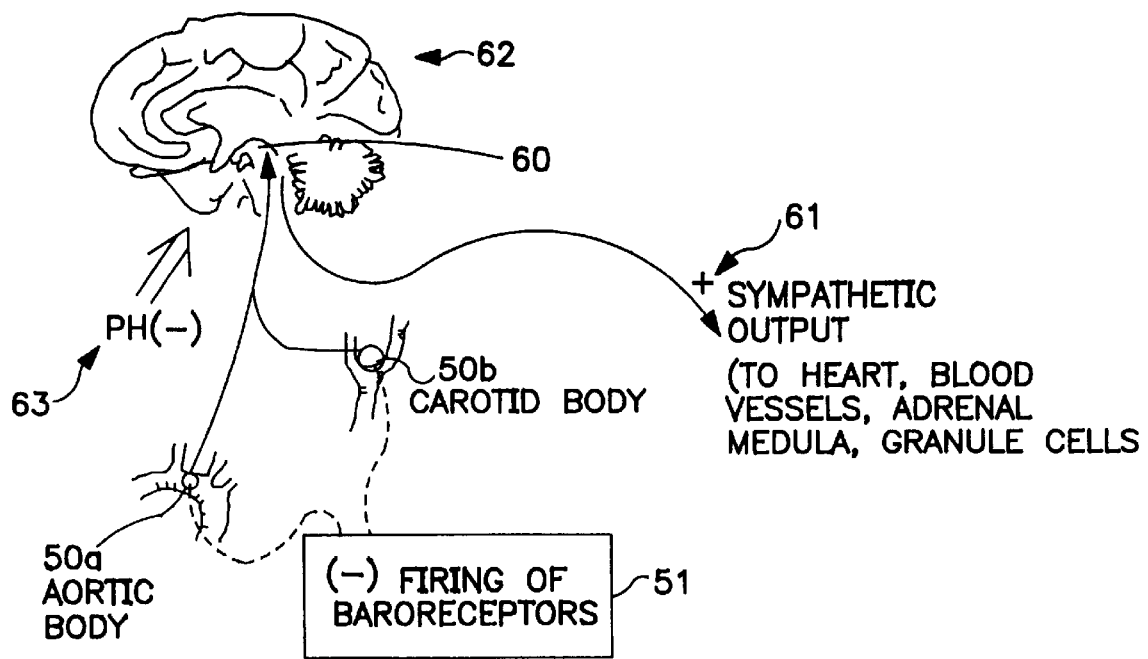
FIG. 2 is a heuristic diagram of the brain and its association to the baroreceptors.

A simplified version of this description is seen in FIG. 2 in which the firing of baroreceptors (50a and 50b) cause stimulation via the cranial nerve 9 and or 10 to reach a reflex arc in the brain stem (60). In any event, stimulation of this reflex produces a decrease in (61) sympathetic output to the heart, blood vessels, adrenal medulla and kidney granule cells. If the baroreceptors are firing less often 51 as in heart failure, the reflex activity is decreased and sympathetic drive is elevated 61. The implanted system would act to counter this reduction in baroreceptor firing and thus decrease the sympathetic drive.

Figure 3:
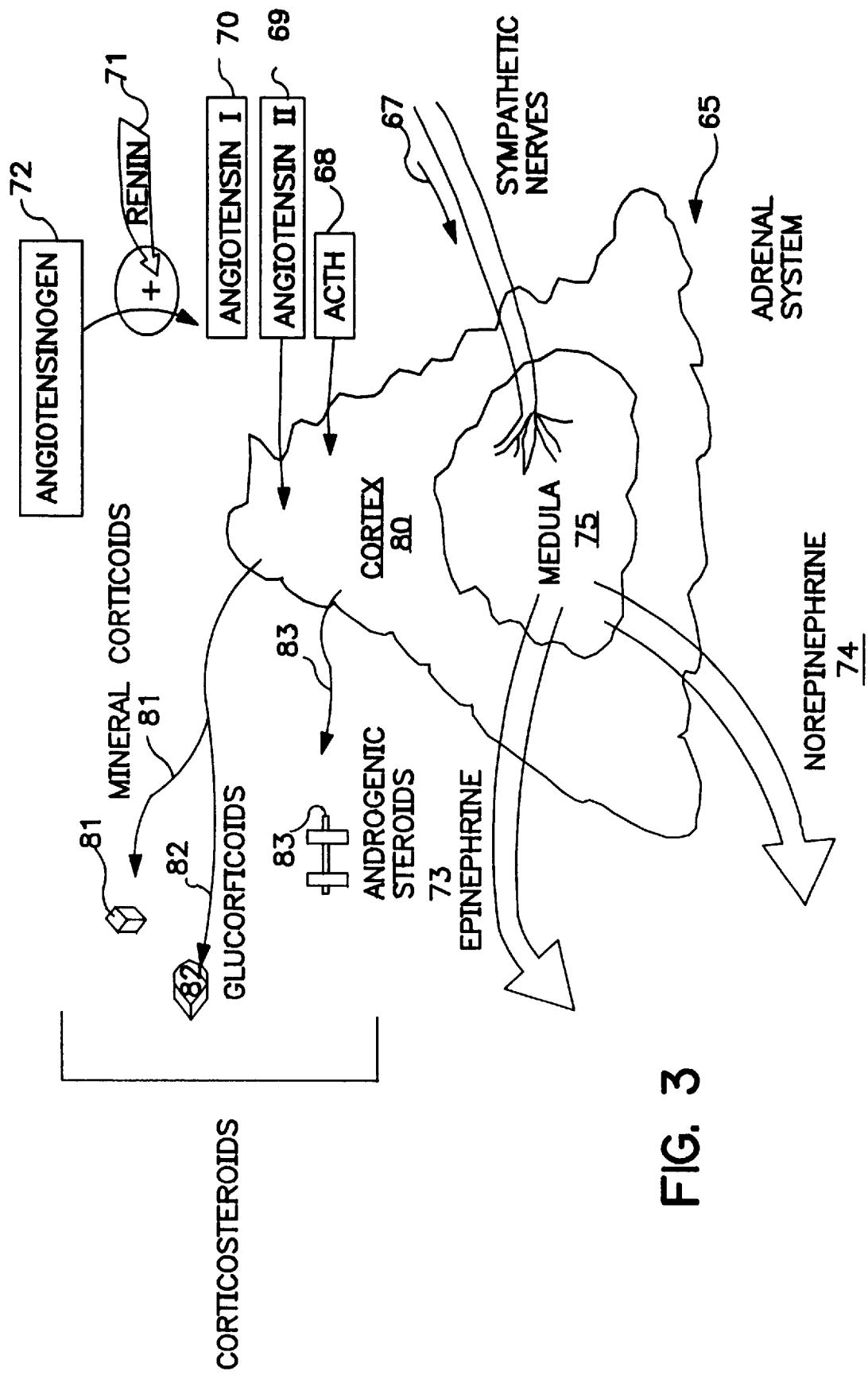
FIG. 3 is heuristic diagram of the adrenal gland and its association with various blood pressure related agents which are found in the blood and in the adrenal gland.

Another major player in this complex homeostatic system is the adrenal gland (FIG. 3, 65). Stimulation of the adrenal medulla (75) by sympathetic nerve (66) impulses (67) causes the adrenal medulla to produce epinephrine 73 and norepinephrine 74. Sympathetic stimulation of the kidney granule cells releases renin (71) which combines with free floating angiotensinogen (72) in the blood stream. This produces angiotensin I (70) and angiotensin II (69) which stimulate the adrenal cortex (80). Adrenocorticotropin hormone or ACTH (68) is a hormone released into the blood by the anterior pituitary due to stress. The angiotensin II and ACTH cause the adrenal cortex (80) to release glucocorticoids 81 as well as mineralocorticosteroids 82 which all generally increase cardiac stress, fluid retention and, blood pressure. Attenuation of the sympathetic drive by the implanted system providing baroreflex stimulation would down-regulate this system leading to a reduction in epinephrine and norepinephrine production, and the release of glucocorticoids and mineralocorticosteroids.

Related systems which may also be affected by the implanted systems would include prostaglandins, the atrial natriuretic factor, ADH secretion by the posterior pituitary which increases vasoconstriction and fluid retention, calcium $CO_2$, lactic acid, hydrogen, potassium, magnesium ions, adenosine, bradykinin and histomem which affect local arterial vascular resistance and Starling's Law. (Starling's Law describes the relationship between cardiac output and cardiac filling.)

Figure 4:
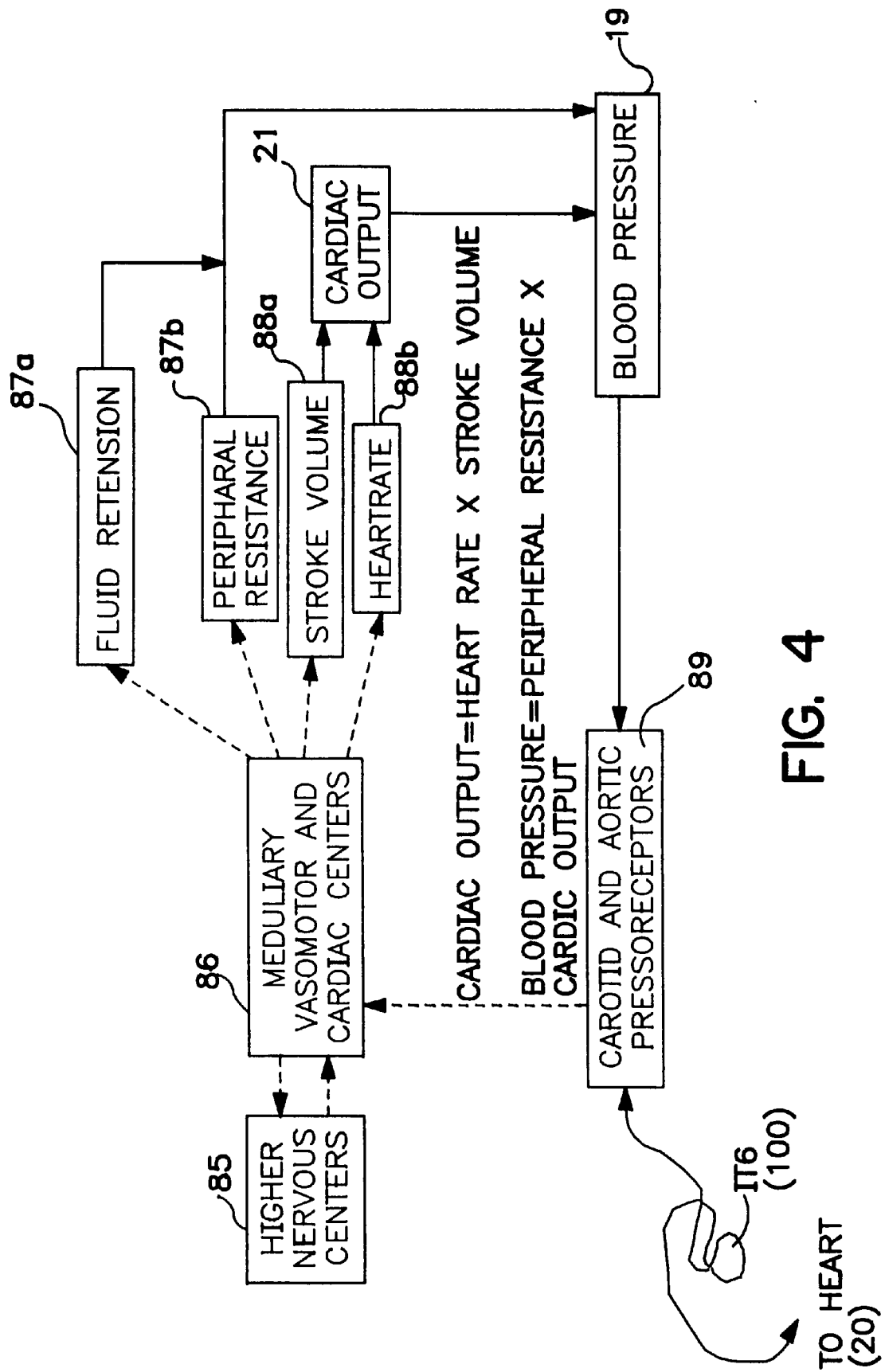
FIG. 4 is a system diagram illustrating the open loop association between an IPG and the patient's blood pressure system.

Influencing these systems through the stimulation of carotid and aortic baroreceptors 89 by implantable pulse generating device 100 can be seen in FIG. 4. In general, the baroreceptors or 89 initiate a reflex arc which involves the medullary vasomotor and cardiac centers 86 which in turn stimulate higher nervous centers 85 with unknown feedback loop effects into the centers 86. The resulting neurohormonal signals affect the fluid retention 87A and peripheral resistance 87B as well as stroke volume 88A and heart rate 88B (The reduction in peripheral resistance act to reduce the blood pressure 19 making it easier for the heart to pump blood into the systemic vasculature.)

Figure 7:
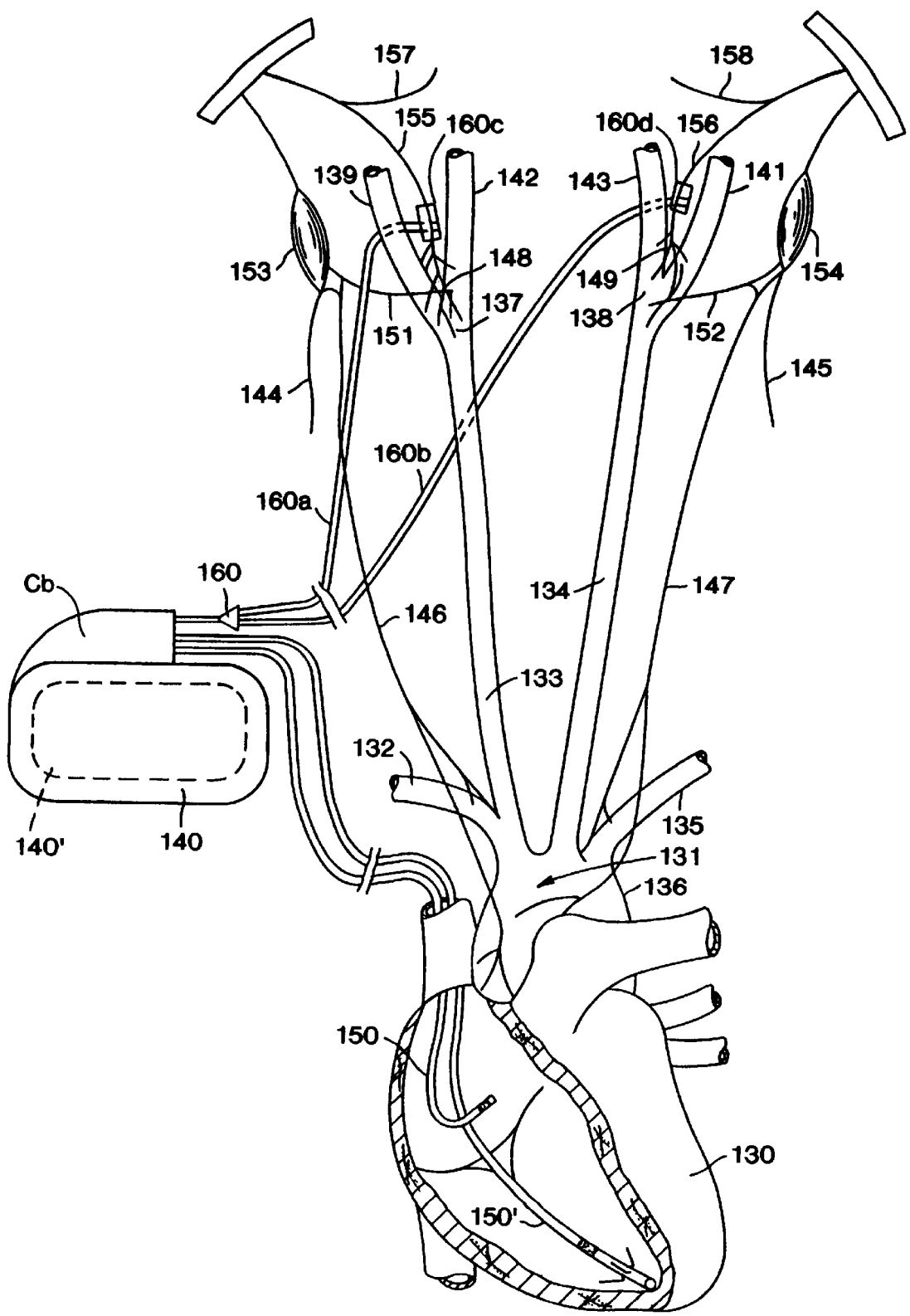
FIG. 7 is an illustration of one preferred embodiment form in an anatomical drawing of the relevant body parts.

It is helpful to discuss the physical system in the body, illustrated in FIG. 7. The heart 130 pumps oxygenated blood out through the aortic arch 131, which leads to the right subclavian artery 132, the right common carotid 133, the left common carotid 134, the left subclavian artery 135, and the thoracic aorta 136. The body's system utilizes stretch receptors located in the arterial walls in the aortic arch 131 and at the bifurcation of the carotid arteries 137, 138 in the carotid sinus portion of the neck. The bifurcation of the carotid arteries 137, 138 leads to exterior carotid arteries 139, 141, respectively, and to interior carotid arteries 142, 143, respectively.

Nerve fibers extending from stretch receptors in the aortic arch 131 join the left and right vagus nerves 144, 145, respectively, with these fibers being referred to as cardiac depressor nerves 146, 147. A number of nerves extend from the stretch receptors at the bifurcation of the carotid arteries 137, 138 in the carotid sinus, with the areas immediately above the bifurcations being referred to as the carotid bodies 148, 149. Nerve branches 151, 152 extending from the carotid bodies 148, 149, respectively, join the ganglia of vagus nerves 153,154, respectively. Other nerve fibers comprising the sinus nerve branches 155, 156, (generally referred to as "Hering's nerves") of the glossopharyngeal nerves, 157, 158, respectively, also extend from the carotid bodies 153, 154, respectively, to the medulla (not shown).

The rate of the heart is restrained by the right and left vagus nerves 144, 145, respectively in conjunction with the cardiac depressor nerves, 146, 147, respectively. The cardio-inhibitory center of the nervous system exerts a tonic effect upon the heart, via the vagus nerves, restraining its rate. This effect is also known as vagal tone.

A pulse generator 140 (which may have an indifferent case electrode 140' for bradycardia support pacing with a unipolar electrode in the heart, or which may use bipolar pacing electrodes) and the system containing the sensing, nerve stimulation and brady pacing pulse generators in accord with the preferred embodiment of this invention is shown in FIG. 7 in relation to the heart 130 and the cardiac nerve system. A lead body 150 coupled to pulse generator 60 extends into the right atrium, but if desired could extend to the coronary sinus. Lead body 150 or the ventricular lead 150' should contain any relevant sensors in the preferred embodiments, however it is not outside the scope of this invention to employ other locations for the sensors ($SVO_2$, pH, transventricular or other impedance, heart sounds, etc.) as may be in accord with the preference of the designer of a system based on this invention. The second lead 150' extends from the pulse generator 140 through the right atrium and into the right ventricle of the patient's heart to position the tip deep within the ventricular apex. The positioning of such leads and their use with and without extra sensors in the heart is well known.

A second pair of electrical leads 160a and 160b extend from the connector block CB of the pulse generator to respective nerve electrodes 160c and 160d placed around the right and/or left carotid sinus nerve bodies in a manner such as that described, for example, in U.S. Pat. Nos. 3,421,511 and 3,522,811. Although other attachment means may be used if desired. It is currently understood that in general nerve stimulation requires a bipolar electrode. In this document we just call such nerve stimulation connections merely "electrodes" or "leads".

The specific location of the nerve electrodes may vary, and it is contemplated that in the practice of the present invention it may be possible to place such electrodes at the right and/or left stellate ganglions (153 and 154). Alternatively, it is possible to extend a single lead electrode from the pulse generator to a dorsal column stimulating electrode. Such an electrode (not shown) may be positioned in the epidural space roughly at level $T_2$ and may be of the type sold by Medtronic, Inc. as part of the Resume IIä and Picses-Sigmaä electrode system or described in Medtronic U.S. Pat. No. 4,414,986 and other Medtronic patents referenced therein.

If a pH sensor is used on the lead, one such as that described in U.S. Pat. Nos. 4,009,721, 3,577,315, 3,658,053, 3,710,778 may be used. A membrane pH sensor electrode is typically placed in the right ventricle and senses pH, which is proportional to the blood concentration of carbon dioxide, which in turn is generated in increasing amounts by exercise as explained in U.S. Pat. No. 4,716,887. In the '721 patent, a diminution in the pH level is used to produce a higher paced cardiac rate. However, if used in the context of the present invention, it is contemplated that the pH sensor will be placed on lead 150 just inside the coronary sinus (not shown) to detect the level of lactic acid in venous return blood which is expected to increase with exercise of the cardiac muscle, particularly if the muscle is stressed by a lack of sufficient oxygen due to constriction in the cardiac arteries as a result of coronary artery disease. Myocardial ischemia is virtually invariably associated with an increase in the blood lactic acid level in the coronary sinus. The increase in blood lactic acid level is accompanied by a decrease in pH. Because of the difficulty of insertion of leads into the coronary sinus, however, we prefer to use the pressure and $SVO_2$ sensor configuration with the leads positioned as shown.

A dissolved blood oxygen sensor may be of the type described in Medtronic U.S. Pat. Nos. 4,750,495, 4,467,807 and 4,791,935. There, an optical detector is used to measure the mixed venous oxygen saturation.

A dual chamber pacemaker is preferred but the invention could also be practiced with alternatives to this. For example, if a better measure than estimated PVR is used(see below), such as a direct SVR measurement (say, from in the peripheral vasculature), some of the usefulness of the ventricular sensors is supplanted. However, since it is possible (because of the nerve stimulation and body response to it) to throw the patient into a situation where he responds with AV block, the ventricular pacing lead remains quite important in any configuration.

The cardiac output 21 is thus is reduced by baroreceptor stimulation. It seems contradictory that decreasing the cardiac output would help hemodynamically impaired heart failure patients. However, heart failure patients have a deleteriously high level of sympathetic drive keeping their hearts under stress to pump harder and faster while the effect is to exacerbate the cause of the heart failure. The body will compensate for the temporarily lowered cardiac output, and removing the vicious cycle of increased sympathetic drive will help to alleviate CHF related problems.

Figure 5:
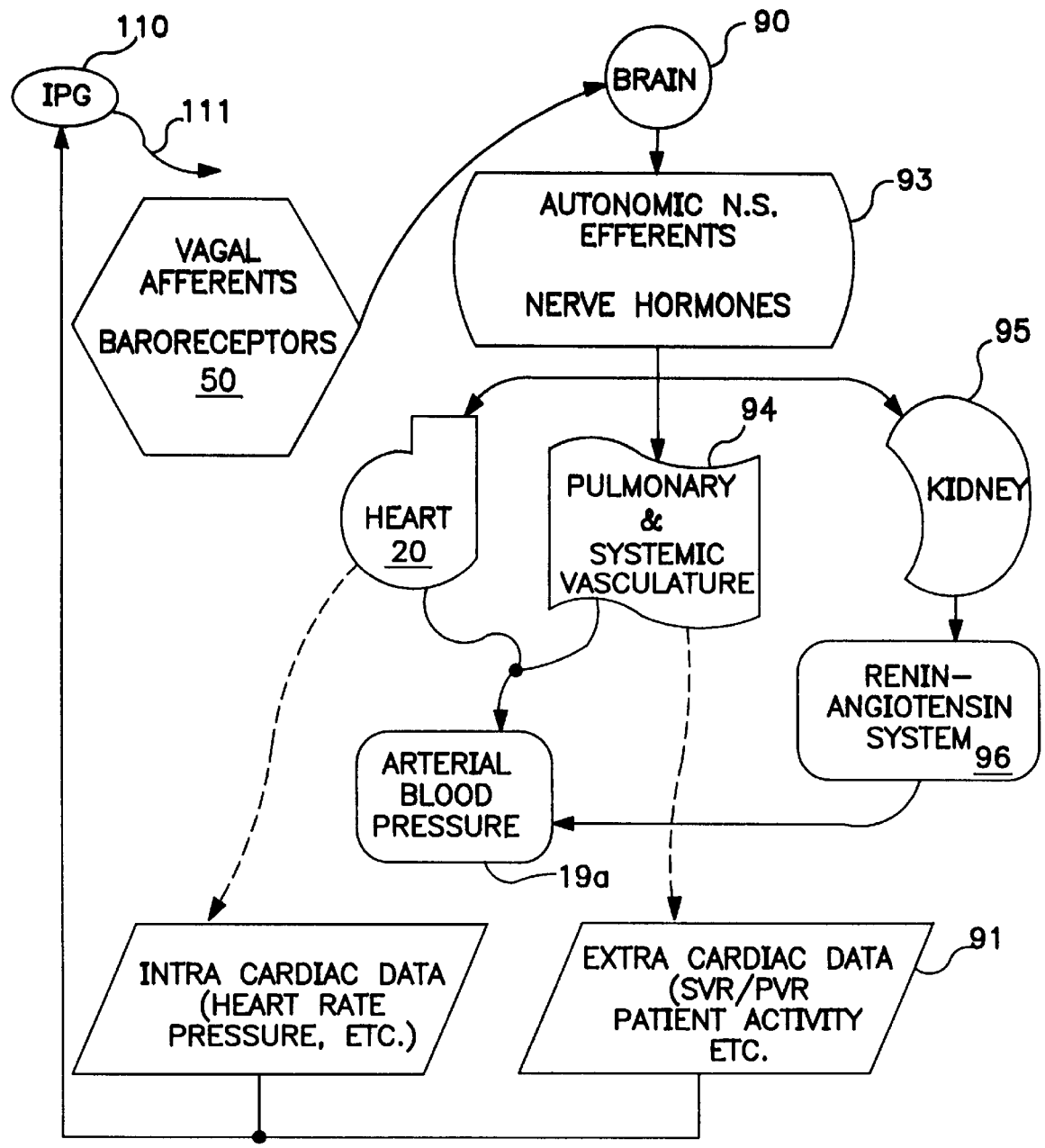
FIG. 5 shows a closed loop system similar to the system of FIG. 4.

An alternate depiction of the system and its interactions with the body is shown in FIG. 5. Again, the nerves arising from the baroreceptors (50) are stimulated (111) by the IPG (110) which activates the reflex in the brain (90) and affects the efferent autonomic nervous system (93) with effects on the heart (20), vasculature (94) and kidneys (95). These systems net effects act on the arterial blood pressure (19a) which affects the level of baroreceptor stimulation which occurs naturally. A preferred embodiment has one or two intracardiac leads which collect signals (92) such as heart rate, pressure, etc. and sensors for extracardiac signals such as the systemic vascular resistance (91) and others may also be monitored. These signals feed back into the IPG (91f and 92f) which can then modulate the stimulation to meet the patient's needs. A preferred embodiment would include an activity sensor such as a piezoelectric crystal for sensing vibration caused by exercise. This sensor would also act as a feedback inhibitory mechanism (91f) to reduce the level of baroreflex stimulation. During periods of exercise, the body acts to increase the rate and strength of myocardial contraction raising the blood pressure to meet the body's increased need. Countering this increase in blood pressure with baroreflex stimulation would not be advantageous during exercise as it would limit the patient's exercise capacity. Therefore, this feedback mechanism would prevent overstimulation during periods of exercise when an increase in blood pressure is physiologically necessary.

Figure 6:
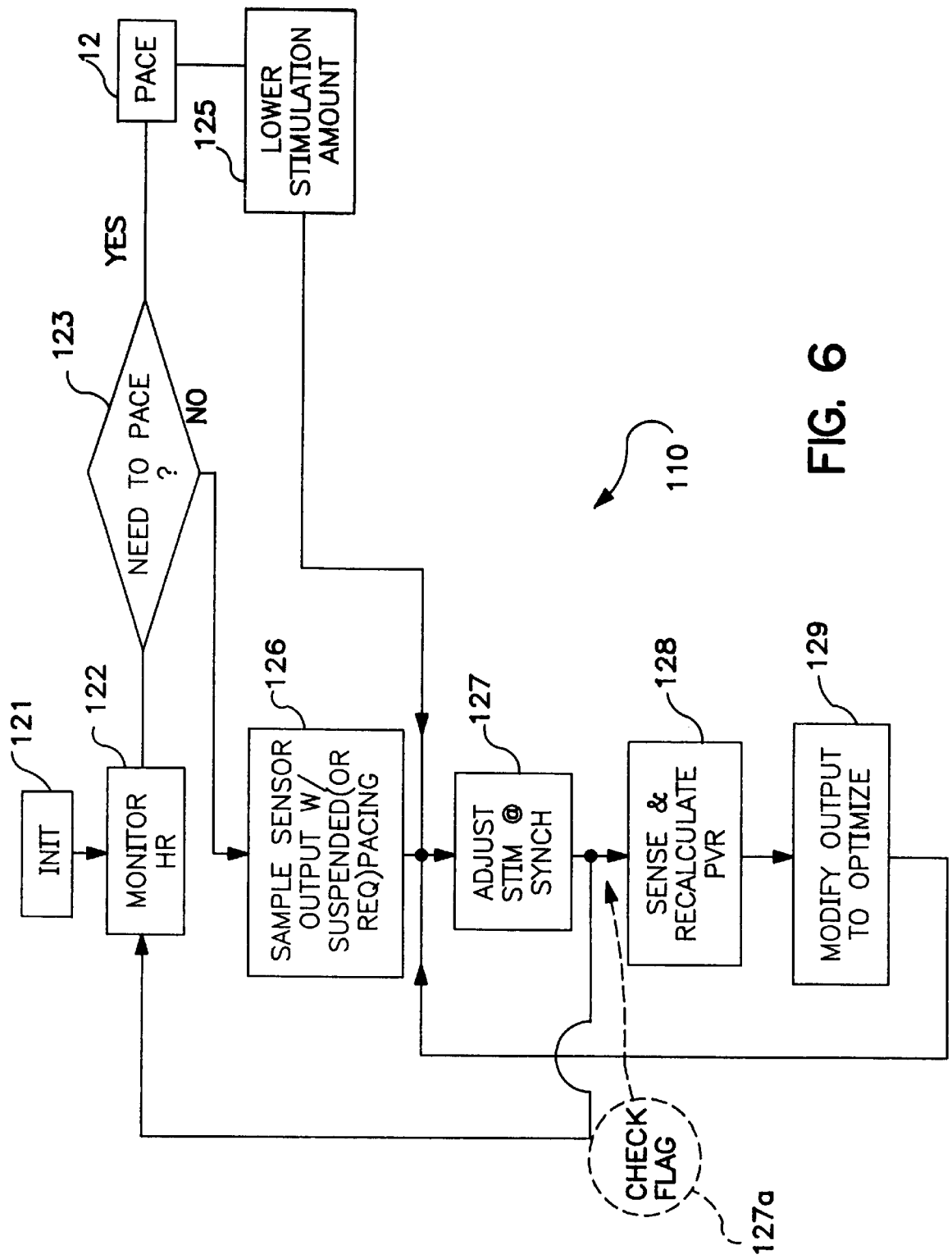
FIG. 6 is a flow diagram illustrating the preferred embodiment configuration of steps associated with the control of the cardiovascular regulatory centers in association with an implanted IPG in accord with the present invention.
Figure 8:
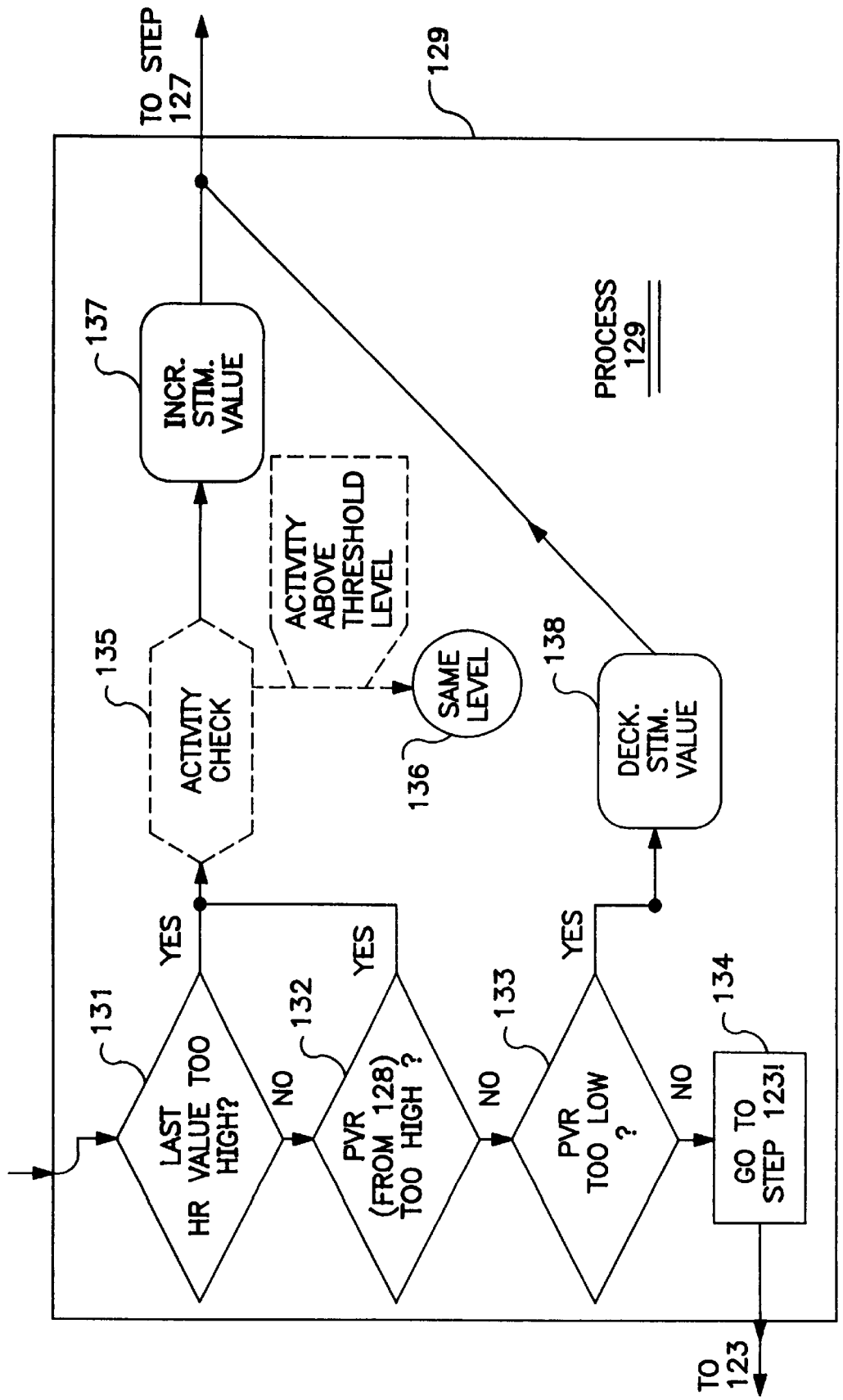
FIG. 8 is a flow chart illustrating process step 129 of FIG. 6.

FIGS. 6 and 8 are is used to illustrate the inventive method 110 for operation of an implanted device that has the capacity to electrically stimulate the baroreflex arc in a living body. The process 110 begins at step (illustrated by a block, here) 121, with the definition of initial parameters and initiation of an algorithm. The rate, pulse width and amplitude, as well as the frequency of the stimulation to the nerve should be set in this step 121. Initial parameter settings can be set by an attending physician, by the factory, or by a program in the programmer that communicates with the implanted device.

In the preferred embodiment, the implanted device (IPG) will monitor the heart rate, at least(step 122), and may monitor other conditions in the body as well, if desired. This step permits the implanted device to decide based on such monitoring whether to vary the initial or later stimulation settings. If the heart rate measured by the device indicates that brady pacing is required (step 123), the device will provide bradycardia back-up pacing via step 124.

This can be determined in a number of ways, generally referred to as overshooting the target rate or range. A body of patent and other literature identifies situations determinable merely through the use of heart rate monitoring by electrographic or other means wherein bradycardia support pacing would be required. For example, in the situation of Vasovagal Syncope, a rapid drop in heart rate provides a good indicator, or if the heart rate falls below a certain predetermined minimum level other pacers begin support pacing.

If pacing is being provided to the body's heart, the level of stimulation provided by the nerve stimulator is generally kept lower than if pacing is not occurring(step 125) as nerve stimulation to the baroreflex arc causes a reduction in the natural heart rate. Again, this can be done in increments or to levels suggested by tables in memory or programmed by the programmer, a physician, or at the factory. (The idea here is that if pacing is required, the heart may be in a condition that is somewhat inadequate and the body is responding by manifesting heart failure. Continuing to stimulate the heart to beat at adequate rhythm while also stimulating vagal tone should reduce the stress on the heart, giving it a chance to recover without incapacitating the body. However, it should be recognized that increasing baroreflex stimulation reduces natural heart rate, and so if it is possible to continue baroreflex stimulation at some level that allows for intrinsic adequate intrinsic heart rhythm, that is the preferred condition to be sought by this series of algorithmic steps.) A flag or counter (127a) can retrigger the algorithm from step 122 to prevent a continuous loop that never rechecks heart rate.

To simulate the baroreflex nerve traffic, stimulation is synchronized to the R-wave of the electrogram, plus an offset would reproduce nerve activation coincident with the arterial pulse. It is believed this is the most effective manner of stimulation. Thus, reduced energy expenditure may be possible by using the natural rhythm to time the stimulus pulses. This step is represented by block 127, which shows adding a predetermined value to the receipt of the R wave signal of the ECG to time the release of the next stimulation pulse or pulse burst.

Step 128 calculates an estimated value of systemic vascular resistance (SVR) as a control parameter for stimulation. We make the assumption that changes in SVR parallel changes in pulmonary vascular resistance (PVR), or at least that the changes in one have a close and probably linear relationship to the other. Therefore since an estimate of PVR can be calculated from pressure and oxygen saturation readings taken by a sensor or sensors, we can determine a value for SVR from that. It should be recognized that any sensor set providing sufficient data for determining PVR or SVR would be useful in the context of this invention.

In the currently preferred embodiment we can use well known measurement techniques to find and define the PVR:SVR relationship in the hospital and set this into the IPG memory for use in the following computations. In other words, this comparison of SVR and PVR would be doing a one-time calibration. However, the use of direct SVR measurements (which may someday become readily and available to the IPG) can be used to alter this relationship constant over time and is contemplated as a use of this invention.

PVR is equal to the difference between the mean pulmonary artery pressure ($PA_{mean}$) and mean left atrium pressure ($LA_{mean}$) divided by the cardiac output (CO) as described in the following formula:

$$PVR = (PA_{mean} - LA_{mean})/CO \quad (1)$$

$Pa_{diastolic}$ can be calculated from the right ventricle at the time of pulmonary valve opening as described in U.S. Pat. No. 5,368,040 issued to Carney. The mean pressure can then be calculated by estimating that $Pa_{systolic}$ is approximately equal to the $RV_{systolic}$ pressure and that PA mean is described as the following functions:

$$RV_{systolic} = PA_{systolic} \quad (2)$$

$$PA_{mean} = \tfrac{1}{3} PA_{systolic} + \tfrac{2}{3} PA_{diastolic} \quad (3)$$

Using the method described by Carney, we can also estimate the $LA_{mean}$ from pressures taken in the right ventricle. Thus equation #1 only needs an estimate of CO in order to be solved. CO can be estimated from the mixed venous oxygen saturation levels ($SVO_2$) in the RV as measured by an oxygen sensor associated with the heart according to the following relationship:

$$CO=m(SVO_2)+b \qquad (4)$$

where m and b are constants to be determined from physiologic testing. Such testing can be done on an ongoing basis as mentioned above with reference to possible SVR data but at the present time it is preferred that it be done while the patient is in the hospital and m and b values left at such settings as indicated unless a problem develops. Therefore equation 1 can be solved for PVR. It should be noted that the process described in FIG. 6 may use an alternative from PVR if available from the implanted system in use. Also other relationships developed to replace equation 4 may be substituted and appropriate sensor measurements taken as such developments occur in this field without deviating from the scope of this invention.

(Note to readers: The terms SVR and PVR in other contexts is often used differently but for this document SVR always means systemic vascular resistance and PVR always means pulmonary vascular resistance. The most common other usage is of PVR to mean peripheral vascular resistance which it does not mean in this document.)

Optimization can be based on an analysis of heart sounds, MRI data (in hospital, probably), transventricular impedance, or other indicators of cardiac output and still use the formulation described for SVR or PVR as described above for Block 128. As technologies improve, new sensors will become available to make this possible and economically feasible.

While we prefer to use cardiac output measures, other indicators of cardiovascular health/responsiveness may eventually be proven to be more accurate. Accordingly, we contemplate use of a block similar to block 128 that may adjust optimization based on other parameters such as pH of venous return blood, (an indirect measure of oxygen saturation) or ST segment variation, (an indirect of indication of heart tissue ischemia). What we are hoping to determine is whether the heart is pumping sufficient blood to maintain the body, and if not, to allow for reduced stimulation of the baroreflex so as to protect the patient while lowering cardiac stress as much as possible.

In FIG. 8 the process of step 129 is detailed. Input from 128 goes to step 131 which determines whether or not the heart rate value is too high. If it is, this provides an indication that the stimulation should be increased (i.e., through step 137), however additional factors may be considered. In the preferred embodiment of the invention a rate responsive pacer is used and a sensor for determining the amount of patient activity is employed. This takes place in step 135 "activity check." If the patient activity level is above a predetermined threshold level, the same level of stimulation will be maintained (step 136). It is possible to improve on this algorithm as well by accelerating the rate of increase of stimulation or not according to some preprogrammed set of values. However, we do not have sufficient experience with this system at this time to suggest what the best alternative is for adjusting the stimulation level based on the activity level. However, we can recommend that nerve stimulation be lowered when activity sensing shows the need for greater cardiac output, such as during indicated strenuous activity of the body.

If the heart rate value is not too high, the second determining step 132 is made. The PVR value determined in step 128 is first checked to determine whether it is too high. If it is, then again the nerve stimulation value should be increased 137 and again the activity level checked to modify this increase if necessary or preferred 136.

In step 133 the PVR level may be determined to be too low. If so, the level of stimulation to the baroreceptor nerves should be decreased (step 138). If the PVR value is neither too high nor too low, the algorithm should exit process 129 for step 123 to make a determination of whether there is a need to pace. Again, the need to pace would be determined based on whether the heart rate was too low or whether there was some other indication such as vasovagal syncope being detected in the heart. Referring back to FIG. 6, if pacing is required (step 124) the stimulation level again will be lowered (step 125).

As will occur to the reader there are numerous applications for the inventive concepts described herein, however the scope of the invention is only limited by the following appended claims.

We claim:

1. A system for coordinating the stimulation of nerves for controlling the level of neurohormonal activation in a living body having a heart subject to potential or actual pathologic stress levels comprising:

an implantable pulse generator with a microprocessor and memory adapted and disposed to run a plurality of processes, a sensor for sensing $SVO_2$ in the body, and a sensor for determining pressure in a ventricle of the heart of the body, both said sensors adapted and disposed to provide readings to said microprocessor for use by said processes, a bradycardia pacer control process included within said pulse generator for pacing the heart when a condition of bradycardia is present so as to prevent insufficient heart rate by said heart, at least one stimulation electrode connected to effectively deliver electrical stimulation to a baroreceptor nerve site, an adjustment process for monitoring heart rate and estimating PVR from said $SVO_2$ and pressure so as to determine appropriate modifications to the stimulation output to said stimulation electrode, and means for making said modifications.

2. A system as set forth in claim 1 wherein said pulse generator comprises a pacing lead in an atrium and in a ventricle of the heart.

3. A system as set forth in claim 1 wherein said pulse generator comprises separate pacing leads in the atrium and the ventricle.

4. A system as set forth in claim 1 wherein said pulse generator comprises an activity sensor associated therewith which provides data on cardiac demand to said pacer control process.

5. A system as set forth in claim 1 wherein said pulse generator has an activity sensor associated therewith which provides data on cardiac demand to said pacer adjustment process.

6. A system as set forth in claim 1 wherein said sensor for determining pressure provides an indication of sensed absolute pressure.

7. A system for coordinating the stimulation of nerves for controlling the level of neurohormonal activation in a living body having a heart subject to potential or actual pathologic stress levels comprising:

an implantable pulse generator with a microprocessor and memory adapted and disposed to run a plurality of processes, a sensor for sensing and measuring the value of an indicator of SVR in said body, adapted and disposed to provide readings to said microprocessor for use by said processes, a bradycardia pacer control process included within said pulse generator for pacing the heart when a condition of bradycardia is present so as to prevent insufficient heart rate by said heart, at least one stimulation electrode connected to effectively deliver electrical stimulation output to a baroreceptor nerve site, a process for monitoring heart rate and estimating SVR from said sensor in order to modify said stimulation output.

8. A system as set forth in claim 7 wherein said indicator for determining SVR is right ventricular pressure.

9. A system as set forth in claim 7 wherein said indicator for determining SVR is $SVO_2$.

10. A system as set forth in claim 7 wherein said indicator for determining SVR is a combination of $SVO_2$ and right ventricular pressure.

11. A system as set forth in claim 10 wherein said process for estimating SVR bases that estimate on the relationship of SVR to PVR and determines PVR based on measured $SVO_2$ and right ventricular pressure.

12. A system as set forth in claim 7 wherein said process for estimating SVR increases said stimulation output at a predetermined level of estimated SVR and decreases said stimulation output at another predetermined level of estimated SVR.

13. A system as set forth in claim 12, further comprising an activity sensor, wherein said process for estimating SVR comprises a check of the activity sensor level made before increasing said stimulation output.

14. A system as set forth in claim 12 further comprising an additional process within said pulse generator wherein if the estimated SVR is not determined to be above a predetermined level nor below another predetermined level, said additional process determines whether pacing is needed, and if so provides for a decreased amount of said stimulation output.

15. A system as set forth in claim 7 wherein if said activity sensor indicates strenuous exercise, said stimulation output is suspended for the duration such indication is present.

16. A system as set forth in claim 7 further comprising an intracardiac electrode and an additional process within said pulse generator, wherein said additional process provides that said stimulation output is gated to electrocardiographic indicators of cardiac activity received by said intracardiac electrode.

17. A system as set forth in claim 16 wherein said additional process provides comprises variable stimulation output settings and delay timing.

18. A method of automatically optimizing the cardiovascular responsiveness of a patient for the patient's condition through controlled application of electrical stimulation of nerves emanating from baroreceptors of said patient comprising:

providing electrical stimulation to said nerves of sufficient intensity and duration so as to reduce neurohormonal activation and induce peripheral blood vessel dilation and a drop in heart rate, determining the responsiveness of the patient's body to said stimulation by sensing a feedback parameter of patient's responsiveness indicating altered cardiovascular function; and adjusting said electrical stimulation provided to the nerves based on said feedback and an optimization algorithm until the patient's cardiovascular system is optimized for his/her condition, sensing activity of said patient using an activity sensor, and if said activity sensor indicates periods of activity, suspending or lowering intensity of said electrical stimulation until a period of time after the sensed activity has ceased.

19. A method as set forth in claim 18 wherein when the optimization algorithm is informed of overshoot in the drop in heart rate and/or peripheral vascular resistance responding by reducing the stimulation of the nerves arising from the baroreceptors.

20. A method as set forth in claim 19, wherein if overshoot of drop in heart rate passes a predetermined threshold, pacing the heart to maintain a predetermined heart rate.

21. A method of controlled application of electrical stimulation of nerves emanating from baroreceptors of said patient comprising:

providing electrical stimulation to said nerves of sufficient intensity and duration so as to reduce neurohormonal activation and induce peripheral blood vessel dilation and a drop in heart rate, sensing activity of said patient using an activity sensor, and if said activity sensor indicates periods of activity, suspending or lowering intensity of said electrical stimulation until a period of time after the sensed activity has ceased.

* * * * *

UNITED STATES PATENT AND TRADEMARK OFFICE
CERTIFICATE OF CORRECTION

PATENT NO. : 6,073,048
DATED : June 6, 2000
INVENTOR(S) : Kieval et al

It is certified that error appears in the above-identified patent and that said Letters Patent is hereby corrected as shown below:

<u>Title page,</u>
Item [75] Inventors: "Tom D. Bettett" should read -- Tom D. Bennett --

Signed and Sealed this

Sixth Day of November, 2001

Attest:

*Nicholas P. Godici*

NICHOLAS P. GODICI
*Attesting Officer*    *Acting Director of the United States Patent and Trademark Office*